United States Patent
Chan et al.

(10) Patent No.: US 8,366,667 B2
(45) Date of Patent: Feb. 5, 2013

(54) FLOW PULSATILITY DAMPENING DEVICES

(75) Inventors: William Chan, Pomfret Center, CT (US); Ramiro Castellanos, Waukesha, WI (US); Reema A. Bhagtani, Milwaukee, WI (US); Georgios A. Bertos, Chicago, IL (US); Rongsheng Lin, Buffalo Grove, IL (US); Richard Boyer, Evanston, IL (US); Jorge DelCastillo, Des Plaines, IL (US); Gary Schultz, Libertyville, IL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 0 days.

(21) Appl. No.: 12/704,214

(22) Filed: Feb. 11, 2010

(65) Prior Publication Data

US 2011/0196303 A1   Aug. 11, 2011

(51) Int. Cl.
*A61M 37/00* (2006.01)
*A61M 1/00* (2006.01)
*A61M 31/00* (2006.01)

(52) U.S. Cl. .................... 604/132; 604/67; 604/153

(58) Field of Classification Search ............. 604/65, 604/67, 132, 133, 140, 141, 151–153, 246, 604/890.1
See application file for complete search history.

(56) References Cited

U.S. PATENT DOCUMENTS

| | | |
|---|---|---|
| 422,936 A | 3/1890 | Hanson |
| 1,627,257 A | 5/1927 | Stevens |
| 2,307,566 A | 1/1943 | Browne |
| 2,315,179 A | 3/1943 | Allender |
| 2,393,838 A | 1/1946 | Tarbox |
| 2,474,512 A | 6/1949 | Bechtold et al. |
| 2,565,374 A | 8/1951 | Kitchel |
| 2,773,455 A | 12/1956 | Mercier |
| 2,927,658 A | 3/1960 | Slater, Jr. |
| 3,252,623 A | 5/1966 | Corbin et al. |
| 3,527,700 A | 9/1970 | Goldhaber |
| 3,658,445 A | 4/1972 | Pulman et al. |
| 3,741,692 A | 6/1973 | Rupp |
| 3,778,195 A | 12/1973 | Bamberg |
| 3,804,107 A | 4/1974 | Kozlov et al. |

(Continued)

FOREIGN PATENT DOCUMENTS

| | | |
|---|---|---|
| DE | 1960369 A1 | 6/1971 |
| EP | 0 816 677 | 1/1998 |

(Continued)

OTHER PUBLICATIONS

International Search Report and Written Opinion for International Application No. PCT/US2009/030299 mailed on May 29, 2009.

(Continued)

*Primary Examiner* — Victoria P Shumate

(74) *Attorney, Agent, or Firm* — K&L Gates LLP

(57) ABSTRACT

A medical fluid infusion system including: a fluid pathway for transporting a pulsatile flow of fluid; a dampening element in communication with the fluid pathway, the dampening element configured to actively dampen pressure fluctuations of the pulsatile flow to smoothen the pulsatile fluid flow, the dampening element operable in any orientation; and a fluid flow sensor disposed along the fluid pathway downstream of the dampening element to measure the flow rate of the smoothened fluid flow.

8 Claims, 6 Drawing Sheets

U.S. PATENT DOCUMENTS

| | | | |
|---|---|---|---|
| 3,818,934 | A | 6/1974 | Borsanyi |
| 3,902,490 | A | 9/1975 | Jacobsen et al. |
| 3,974,854 | A | 8/1976 | Kurpanek |
| 3,986,956 | A | 10/1976 | Anno |
| 4,003,379 | A | 1/1977 | Ellinwood, Jr. |
| 4,077,405 | A | 3/1978 | Hoerten et al. |
| 4,081,372 | A | 3/1978 | Atkin et al. |
| 4,107,039 | A | 8/1978 | Lindsay, Jr. et al. |
| 4,191,184 | A | 3/1980 | Carlisle |
| 4,193,068 | A | 3/1980 | Ziccardi |
| 4,209,014 | A | 6/1980 | Sefton |
| 4,258,711 | A | 3/1981 | Tucker et al. |
| 4,264,287 | A | 4/1981 | Ishida et al. |
| 4,293,961 | A | 10/1981 | Runge |
| 4,345,594 | A | 8/1982 | Bisera et al. |
| 4,360,019 | A | 11/1982 | Portner et al. |
| 4,360,324 | A | 11/1982 | Ohara et al. |
| 4,392,791 | A | 7/1983 | Mandroian |
| 4,445,829 | A | 5/1984 | Miller |
| 4,489,750 | A | 12/1984 | Nehring |
| 4,493,706 | A | 1/1985 | Bolsanyi et al. |
| 4,501,583 | A | 2/1985 | Troutner |
| 4,525,165 | A | 6/1985 | Fischell |
| 4,599,165 | A | 7/1986 | Chevallet |
| 4,604,090 | A | 8/1986 | Reinicke |
| 4,610,702 | A | 9/1986 | Krantz |
| 4,653,987 | A | 3/1987 | Tsuji et al. |
| 4,662,829 | A | 5/1987 | Nehring |
| 4,671,792 | A | 6/1987 | Borsanyi |
| 4,673,391 | A | 6/1987 | Kondo et al. |
| 4,684,368 | A | 8/1987 | Kenyon |
| 4,687,423 | A | 8/1987 | Maget et al. |
| 4,687,468 | A | 8/1987 | Gianturco |
| 4,714,462 | A | 12/1987 | DiDomenico |
| 4,728,265 | A | 3/1988 | Cannon |
| 4,741,678 | A | 5/1988 | Nehring |
| 4,744,786 | A | 5/1988 | Hooven |
| 4,767,526 | A | 8/1988 | Vantard |
| 4,838,887 | A | 6/1989 | Idriss |
| 4,871,351 | A | 10/1989 | Feingold |
| 4,921,477 | A * | 5/1990 | Davis ............... 604/22 |
| 4,954,046 | A | 9/1990 | Irvin et al. |
| 4,969,936 | A | 11/1990 | Schweigert et al. |
| 4,978,338 | A | 12/1990 | Melsky et al. |
| 4,979,441 | A | 12/1990 | Welch et al. |
| 5,053,031 | A | 10/1991 | Borsanyi |
| 5,057,081 | A | 10/1991 | Sunderland et al. |
| 5,088,904 | A | 2/1992 | Okada |
| 5,116,308 | A * | 5/1992 | Hagiwara .................. 604/6.15 |
| 5,152,680 | A | 10/1992 | Okada |
| 5,176,644 | A | 1/1993 | Srisathapat et al. |
| 5,183,974 | A | 2/1993 | Wilhelm et al. |
| 5,244,463 | A | 9/1993 | Cordner, Jr. et al. |
| 5,247,434 | A | 9/1993 | Peterson et al. |
| 5,263,935 | A | 11/1993 | Hessel |
| 5,290,158 | A | 3/1994 | Okada |
| 5,387,188 | A | 2/1995 | Watson |
| 5,421,208 | A | 6/1995 | Packard et al. |
| 5,522,998 | A | 6/1996 | Polaschegg |
| 5,544,651 | A | 8/1996 | Wilk |
| 5,554,011 | A | 9/1996 | Bales et al. |
| 5,562,429 | A | 10/1996 | Romstad et al. |
| 5,607,418 | A | 3/1997 | Arzbaecher |
| 5,730,722 | A | 3/1998 | Wilk |
| 5,817,076 | A | 10/1998 | Fard |
| 5,868,168 | A | 2/1999 | Mott et al. |
| 5,871,478 | A | 2/1999 | Berrigan |
| 6,058,958 | A | 5/2000 | Benkowski et al. |
| 6,089,837 | A | 7/2000 | Cornell |
| 6,159,160 | A | 12/2000 | Hsei et al. |
| 6,234,773 | B1 | 5/2001 | Hill et al. |
| 6,280,408 | B1 | 8/2001 | Sipin |
| 6,290,681 | B1 | 9/2001 | Brown |
| 6,305,919 | B1 | 10/2001 | Staton et al. |
| 6,312,409 | B1 | 11/2001 | Gross |
| 6,319,245 | B1 | 11/2001 | Berrigan |
| 6,386,046 | B1 | 5/2002 | Mattar |
| 6,471,686 | B1 | 10/2002 | Berrigan |
| 6,537,268 | B1 | 3/2003 | Gibson et al. |
| 6,558,343 | B1 | 5/2003 | Neftel |
| 6,638,263 | B1 | 10/2003 | Theeuwes et al. |
| 6,669,455 | B2 | 12/2003 | Welch |
| 6,723,062 | B1 | 4/2004 | Westberg et al. |
| 6,746,606 | B2 | 6/2004 | Pfeil et al. |
| 6,837,693 | B2 | 1/2005 | Welch |
| 6,861,033 | B2 | 3/2005 | Mullins et al. |
| 6,997,942 | B2 | 2/2006 | Machold et al. |
| 7,018,361 | B2 | 3/2006 | Gillespie, Jr. et al. |
| 7,018,375 | B2 | 3/2006 | Berrigan |
| 7,025,750 | B2 | 4/2006 | Brugger et al. |
| 7,048,522 | B2 | 5/2006 | Bradford, Jr. |
| 7,150,711 | B2 | 12/2006 | Nusser et al. |
| 7,175,649 | B2 | 2/2007 | Machold et al. |
| 7,208,092 | B2 | 4/2007 | Micheli |
| 7,241,378 | B2 | 7/2007 | Ikeda |
| 7,326,564 | B2 | 2/2008 | Lundell et al. |
| 7,678,070 | B2 * | 3/2010 | Kumar et al. ............... 604/31 |
| 2002/0088752 | A1 | 7/2002 | Balschat et al. |
| 2002/0127736 | A1 | 9/2002 | Chou et al. |
| 2003/0195454 | A1 | 10/2003 | Wariar et al. |
| 2004/0019320 | A1 | 1/2004 | Childers et al. |
| 2004/0082903 | A1 | 4/2004 | Micheli |
| 2005/0038325 | A1 | 2/2005 | Moll |
| 2005/0070883 | A1 * | 3/2005 | Brown et al. .............. 604/890.1 |
| 2006/0129099 | A1 * | 6/2006 | Kumar et al. .............. 604/151 |
| 2007/0135758 | A1 | 6/2007 | Childers et al. |
| 2007/0158267 | A1 | 7/2007 | Micheli |
| 2008/0015493 | A1 | 1/2008 | Childers et al. |
| 2008/0287887 | A1 * | 11/2008 | Mack et al. .............. 604/247 |
| 2008/0294095 | A1 * | 11/2008 | Zacharias .............. 604/65 |
| 2008/0294098 | A1 * | 11/2008 | Sarkinen et al. .............. 604/67 |
| 2008/0300551 | A1 * | 12/2008 | Schiller et al. .............. 604/220 |
| 2008/0306436 | A1 * | 12/2008 | Edwards et al. .............. 604/67 |
| 2008/0319392 | A1 * | 12/2008 | Angel et al. .............. 604/151 |
| 2009/0069784 | A1 * | 3/2009 | Estes et al. .............. 604/500 |
| 2009/0069785 | A1 * | 3/2009 | Miller et al. .............. 604/500 |
| 2009/0112164 | A1 * | 4/2009 | Reilly et al. .............. 604/151 |
| 2009/0118681 | A1 * | 5/2009 | Molgaard-Nielsen ....... 604/246 |
| 2009/0131859 | A1 * | 5/2009 | DelCastillo et al. .......... 604/65 |
| 2009/0177148 | A1 * | 7/2009 | DelCastillo et al. .......... 604/67 |
| 2009/0177149 | A1 * | 7/2009 | Childers et al. .............. 604/67 |
| 2009/0209921 | A1 * | 8/2009 | Claude et al. .............. 604/246 |
| 2009/0234266 | A1 * | 9/2009 | Solomon et al. ............ 604/6.09 |
| 2009/0259183 | A1 * | 10/2009 | Chong et al. .............. 604/152 |
| 2009/0264824 | A1 * | 10/2009 | Bisch et al. .............. 604/151 |
| 2009/0299289 | A1 * | 12/2009 | Kamen et al. .............. 604/151 |
| 2010/0010447 | A1 * | 1/2010 | Luther et al. ............. 604/167.03 |
| 2010/0037680 | A1 * | 2/2010 | Moberg et al. .............. 73/37 |
| 2010/0076412 | A1 * | 3/2010 | Rush et al. .............. 604/890.1 |
| 2010/0094218 | A1 * | 4/2010 | Kriesel et al. .............. 604/132 |
| 2010/0114026 | A1 * | 5/2010 | Karratt et al. .............. 604/151 |
| 2010/0114028 | A1 * | 5/2010 | Rush et al. .............. 604/151 |
| 2010/0114040 | A1 * | 5/2010 | Schriver et al. .............. 604/246 |
| 2010/0228196 | A1 * | 9/2010 | Wyss .............. 604/151 |
| 2011/0060284 | A1 * | 3/2011 | Harr .............. 604/153 |
| 2011/0092894 | A1 * | 4/2011 | McGill et al. .............. 604/29 |
| 2011/0106010 | A1 * | 5/2011 | Steinbach et al. .......... 604/140 |
| 2011/0112488 | A1 * | 5/2011 | Shu .............. 604/246 |

FOREIGN PATENT DOCUMENTS

| | | |
|---|---|---|
| GB | 880192 A | 10/1961 |
| GB | 2181494 | 4/1987 |
| GB | 2303925 A | 3/1997 |
| WO | WO8401718 A1 | 5/1984 |
| WO | 2005/025726 | 3/2005 |
| WO | 2006/008866 | 1/2006 |
| WO | WO2009065153 A2 | 5/2009 |

OTHER PUBLICATIONS

International Search Report and Written Opinion for PCT/US2008/066101 mailed Feb. 12, 2009.

Non-Final Office Action for U.S. Appl. No. 11/941,840 dated Jul. 24, 2009.

Final Office Action for U.S. Appl. No. 11/941,840 dated Feb. 8, 2010.

Non-Final Office Action for U.S. Appl. No. 11/941,840 dated Sep. 17, 2010.

Notification of Transmittal of the International Preliminary Report on Patentability for International Application No. PCT/US2009/047585 dated Oct. 12, 2010.
International Search Report and Written Opinion for International Application No. PCT/US2009/047585 dated Feb. 1, 2010.
Non-Final Office Action for U.S. Appl. No. 12/180,324 dated Aug. 12, 2010.
Written Opinion for International Application No. PCT/US2011/023158 dated May 9, 2011.

International Search Report for International Application No. PCT/US2011/023158 dated May 9, 2011.
Notification of Transmittal of the International Preliminary Report on Patentability for International Application No. PCT/US2011/023158 dated Feb. 3, 2012.

* cited by examiner

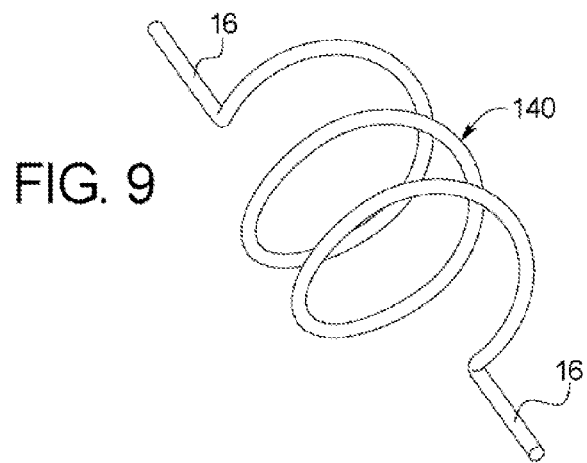
FIG. 9
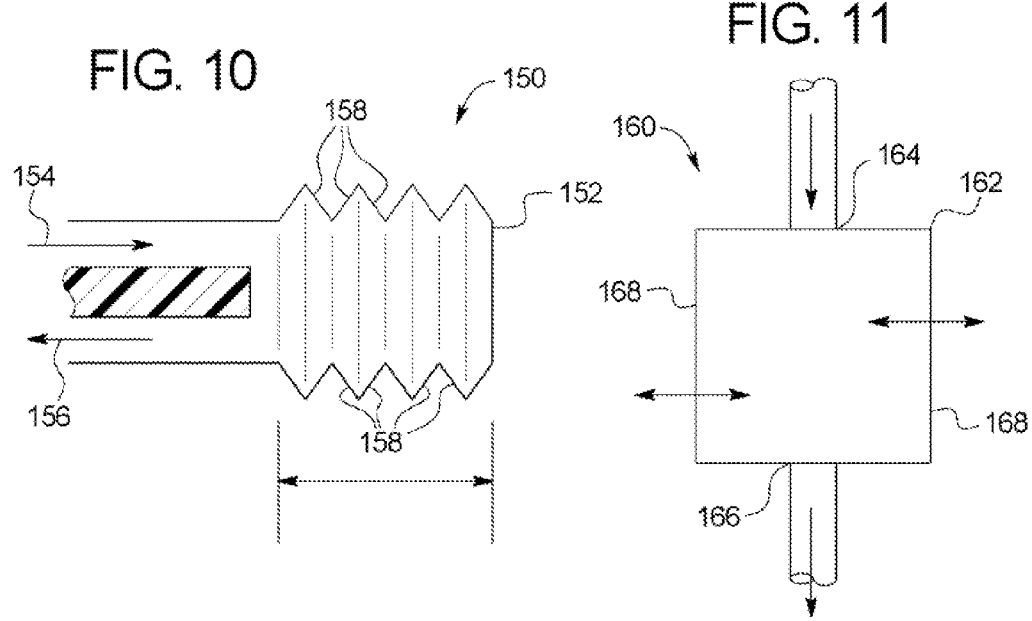
FIG. 10
FIG. 11
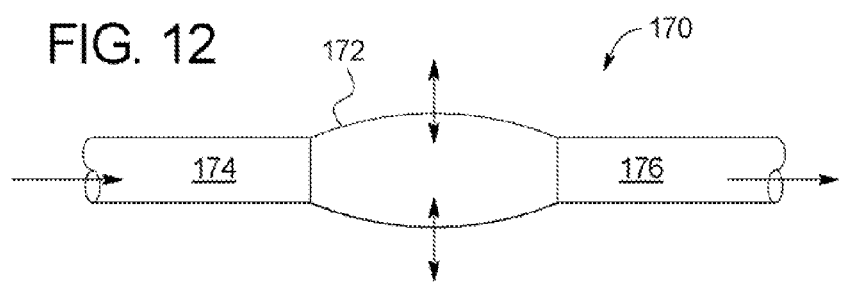
FIG. 12

FLOW PULSATILITY DAMPENING DEVICES

RELATED APPLICATIONS

The present disclosure relates to copending and commonly assigned U.S. patent application Ser. No. 11/941,840, entitled "Flow Pulsatility Dampening Devices For Closed-Loop Controlled Infusion System", filed Nov. 16, 2007.

BACKGROUND

The present disclosure generally relates to medical fluid delivery systems. In particular, the present disclosure relates to devices and methods for transforming a generally pulsatile fluid flow in an infusion system to a smoother or less pulsatile fluid flow.

Liquid medicaments and other complex medical and therapeutic fluids are often administered to patients through infusion therapy. Typically, infusion therapy is accomplished by employing an infusion pump to force fluid through an infusion circuit and into a patient. In certain situations, such as when the infusion of fluid takes place over a long period of time with a patient that is ambulatory, it is desirable to use a disposable infusion system.

Because disposable infusion systems are generally single-use items, such systems typically include relatively simple and inexpensive components. However, one of the difficulties encountered with using relatively simple and inexpensive components is that the components are often not compatible for use with one another. For example, the majority of simple and inexpensive infusion pumps generate a pulsatile or non-continuous fluid flow. Even durable and expensive pumps generate pulsatility. This pulsatile fluid flow is dynamic and has flowrate and pressure fluctuations that change very quickly. Further, most simple and inexpensive fluid flow sensors do not have the temporal resolution or the ability to sense and calculate the flowrate of a pulsatile fluid flow. The incompatibility of these components creates an obstacle to producing economical disposable infusion systems that have the ability to monitor the fluid flowrate within the infusion circuit.

In many infusion therapy applications a fluid is required to be administered to the patient at a certain fluid flowrate to be therapeutically effective. For example, in some applications, if the fluid is infused too slowly, the intended therapeutic effect may be diminished or totally non-existent. In other applications, infusion of a fluid into the body at too high a rate can create a dangerous or overdose situation. Thus, in a number of infusion therapy applications it is important for the user to be able to quickly and accurately determine the rate of fluid flow through the system, so that the flowrate can be monitored and adjusted as needed.

In those instances in which it is important for the user to be able to determine flowrate, a disposable infusion set will often include either an infusion pump that generates a smooth fluid flow or a flow sensor that has the ability to monitor and calculate the flowrate of a pulsatile or non-continuous fluid flow. One of the disadvantages of using a smooth flow generating infusion pump or a flow sensor that can monitor pulsatile flow is that both of those components are relatively expensive and add appreciably to the overall cost of the disposable infusion set. In addition to increased cost, system components that are capable of achieving high resolution measurements often require complex circuitry, hardware and software architecture.

SUMMARY

The present disclosure provides an infusion system that includes a dampening element, which transforms a generally non-continuous or pulsatile flow of fluid within the infusion system into a generally smoother or less pulsatile fluid flow. The incorporation of a dampening element in to an infusion system provides a variety of benefits. For example, the transformation of a generally pulsatile fluid flow into a smoother fluid flow allows a relatively inexpensive fluid flow sensor, which does not have the temporal resolution to sense and calculate flowrate of a pulsatile flow of fluid, to be used to monitor and adjust such fluid flow. The ability to employ a relatively inexpensive flow sensor decreases the overall cost of the infusion system appreciably.

In general, the dampening element is disposed at a location along the fluid pathway of an infusion system and receives a fluid having a pulsatile fluid flow from a fluid source upstream of the dampening element. For example, in one embodiment a medical fluid infusion system of the present disclosure includes a fluid pathway for transporting a pulsatile flow of fluid, e.g., a drug for infusion into the patient pumped from a pulsatile infusion pump, e.g., a membrane pump or a peristaltic pump. A dampening element is placed in fluid communication with the fluid pathway. The dampening element actively dampens pressure fluctuations of the pulsatile flow to smoothen the pulsatile fluid flow. Advantageously, the dampening element can be operated in any orientation and is not gravity dependent. A fluid flow sensor is disposed along the fluid pathway downstream of the dampening element to measure the flow rate of the smoothened fluid flow. The system can provide a common enclosure housing both the dampening element and the fluid flow sensor.

Many different configurations for the dampening element are set forth in detail below. For example, the dampening element can include an outer housing holding air at atmosphere or pressurized from a compressed air source and an inner chamber holding the pumped fluid. Or, the dampening element can include an outer housing holding a rheologiz fluid and an inner chamber holding the pumped fluid. Alternatively, the dampening element includes a bellows that is expanded by the pumped fluid so as to actively provide a compressive force onto the pumped fluid. Further alternatively, the dampening element can include a flexible wall that actively provides a compressive force onto the pumped fluid. Yet further alternatively, the dampening element can include an expandable tube to actively provide a compressive force onto the pumped fluid. In still another alternative embodiment, the dampening element includes a plurality of bunched parallel tubes that actively provide a compressive force onto the pumped fluid.

In particular, one infusion system includes (i) a fluid pathway; (ii) an infusion pump for pumping a non-continuous flow of fluid through the fluid pathway; (iii) a housing enclosing an expandable membrane, an inside of the membrane defining a chamber that is in communication with the fluid pathway, an outside of the chamber within the housing containing a compressible gas that absorbs pressure fluctuations of the non-continuous flowing fluid to smoothen the non-continuous flow, the housing and the chamber operable in any orientation; and (iv) a fluid flow sensor disposed along the fluid pathway downstream of the housing, the fluid flow sensor configured to measure a flowrate of the smoothened fluid flow.

In another embodiment, a medical fluid infusion system includes (i) an infusion pump; (ii) a fluid pathway for transporting a pulsatile flow of fluid produced by the infusion pump; (iii) a fluid holding compartment having an inlet and an outlet in fluid communication with the fluid pathway; (iv) a chamber holding a compressible gas around at least substantially all of an outside surface of the fluid holding compartment so as to tend to dampen fluctuations of the pulsatile flow of fluid; and (v) a flow sensor disposed along the fluid pathway downstream from the fluid holding compartment and the chamber. Here, the inlet and the outlet of the fluid holding compartment can be arranged at least substantially parallel to one another so that the fluid has to change direction after entering the fluid holding compartment. Also, the fluid holding compartment can include an expandable balloon.

In a further embodiment, the medical fluid infusion system includes (i) an infusion pump; (ii) a fluid pathway for transporting a pulsatile flow of fluid produced by the infusion pump; (iii) a fluid holding compartment having an inlet and an outlet in fluid communication with the fluid pathway; (iv) at least one compressible air balloon located inside the fluid holding compartment that tends to dampen fluctuations of the pulsatile flow of fluid; and (v) a flow sensor disposed along the fluid pathway downstream from the fluid holding compartment. Here, the inlet and outlet of the fluid holding compartment can be (a) configured to force the flow of fluid around the at least one compressible air balloon; and (b) arranged with respect to each other such that fluid has to change direction after entering the fluid holding compartment. In one implementation, the fluid holding compartment houses a dividing wall that separates at least two of the compressible air balloons.

In still another embodiment, the medical fluid infusion system includes (i) an infusion pump that creates at least a semi-pulsatile flow of fluid; (ii) a flow sensor disposed downstream from the infusion pump; and (iii) a tube for carrying the at least semi-pulsatile flow of fluid from the infusion pump to the flow sensor, the tube enclosing at least one compressible air balloon for smoothing the flow of fluid from the pump to the flow sensor. In one implementation, the surface of the at least one air balloon is the inner wall surface of the tube.

It is accordingly an advantage of the present disclosure to provide flow dampening for an infusion pump system in which the orientation of the dampening element or dampener is immaterial.

It is another advantage of the present disclosure to provide flow dampening for an infusion pump system in which the dampening element actively dampens pressure fluctuations of the pulsatile flow to smoothen the pulsatile fluid flow.

Additional features and advantages are described herein, and will be apparent from, the following Detailed Description and the figures.

BRIEF DESCRIPTION OF THE FIGURES

FIG. 9 is a schematic view illustrating a sixth embodiment of a flow pulsatility dampening element of the present disclosure.

FIG. 10 is a schematic view illustrating a seventh embodiment of a flow pulsatility dampening element of the present disclosure.

FIG. 11 is a schematic view illustrating an eighth embodiment of a flow pulsatility dampening element of the present disclosure.

FIG. 12 is a schematic view illustrating a ninth embodiment of a flow pulsatility dampening element of the present disclosure.

DETAILED DESCRIPTION

Figure 1:
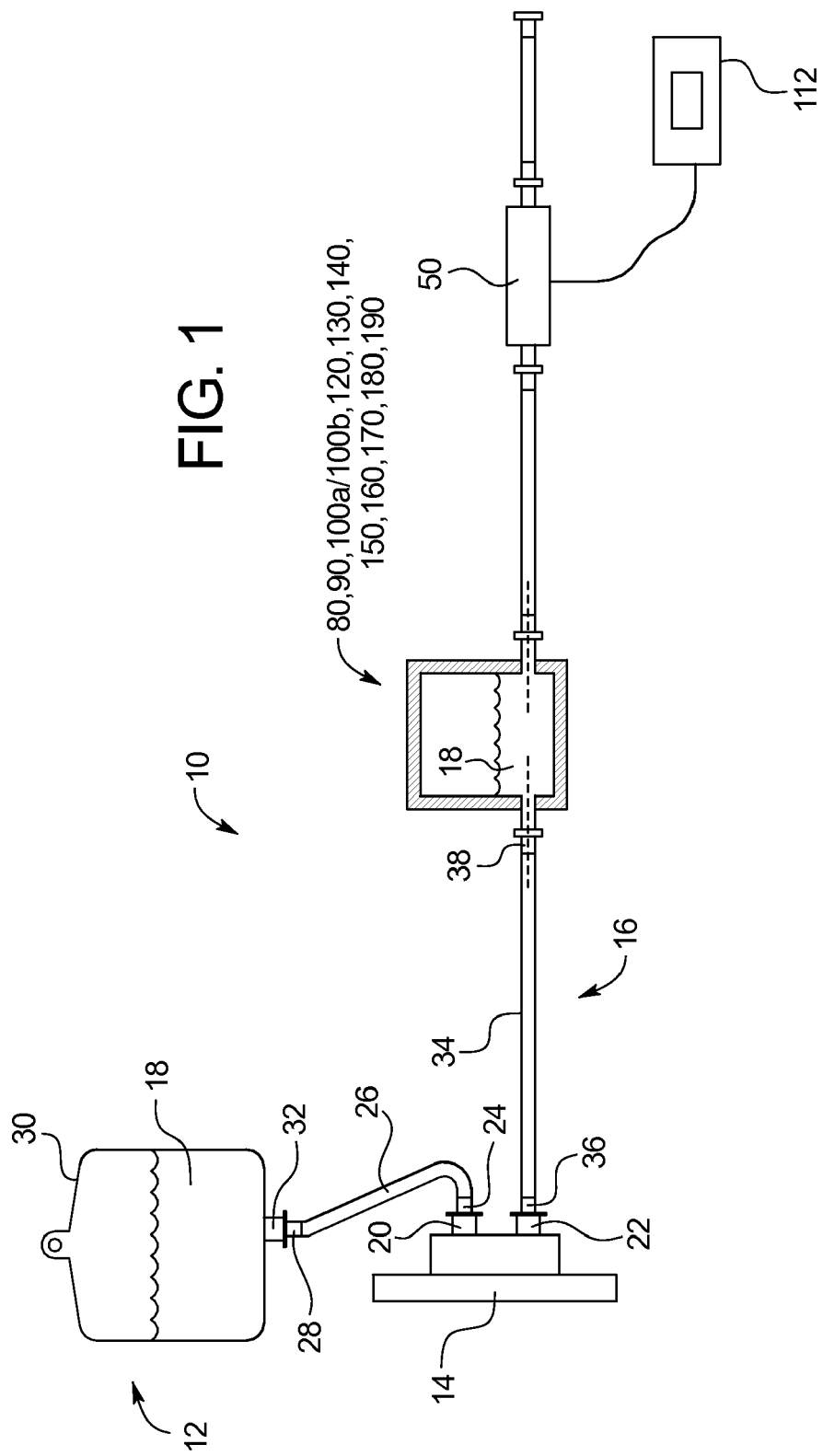
FIG. 1 is a schematic elevation view of one embodiment for placing the various flow pulsatility dampeners in an infusion system according to the present disclosure.

Referring now to the drawings and in particular to FIG. 1, an infusion therapy system or set 10 for infusing fluids, such as medicaments or other therapeutic fluids, into a patient is provided. The infusion therapy system 10 in an embodiment is a disposable infusion system that includes relatively inexpensive component parts. In the embodiment shown, the infusion therapy system 10 includes a fluid supply 12, an infusion pump 14 and a fluid pathway 16. In general, the infusion pump 14 pumps fluid 18 from the fluid supply 12, through the infusion pathway 16, to an infusion device (not shown) that delivers the fluid to a patient. The infusion device can be any number of infusion devices, such as a catheter, implantable port, intravenous delivery device, shunt or other mechanism that interfaces with the patient to deliver fluid.

The infusion pump 14 is a pump that generates a pulsatile fluid flow having pressure fluctuations, such as a micro-diaphragm or a peristaltic pump. For example, the pump can for example be a micro-diaphragm pump provided by thinXXS Microtechnology AG, Zweibrücken, Germany. The pump itself can be disposable. Alternatively, the fluid carrying components of the pump are disposable. These types of pumps are often small in size, generally lightweight and relatively inexpensive. The pump 14 includes an inlet port 20 for receiving fluid and an outlet port 22 for expelling fluid. The inlet port 20 of the infusion pump 14 is connected to the distal end portion 24 of a fluid supply conduit 26, and the proximal end portion 28 of the fluid supply conduit 26 is connected to fluid supply 12. The connection between the fluid supply conduit 26 and the pump 14, and other connections of components described herein, can be any suitable type of permanent or removable connection known to those skilled in the art, such as a male-female luer type connection or an integral connection.

The fluid supply 12 may include a flexible dispensing bag 30 containing a fluid 18 to be infused into the patient. The dispensing bag 30 in an embodiment is made from a polymeric material and includes outlet port 32 that is connected to the proximal end portion 28 of fluid supply conduit 26. The dispensing bag 30 supplies the fluid 18 through the fluid supply conduit 26 to the infusion pump 14.

Infusion pathway 16 provides a fluid path from the pump 14 to an infusion device such as a cannula or catheter (not shown). Infusion pathway 16 can include a first fluid conduit 34 that has a proximal end portion 36 and a distal end portion 38. Proximal end portion 36 of first fluid conduit 34 is connected to outlet port 22 of infusion pump 14 and receives a pulsatile flow of fluid from the infusion pump. For example, the rollers of a race of a peristaltic pump create a generally pulsatile flow. The back and forth motion of a membrane or diaphragm in a membrane pump also creates non-continuous or pulsatile flow.

A pulsatility dampening device or element (referring to any of the dampeners 80, 90, 100a/100b, 120, 130, 140, 150, 160, 170, 180 and 190 described herein) is disposed along infusion pathway 16 at a location that is downstream of the infusion pump 14. Distal end portion 38 of first fluid conduit 34 is connected to the dampening element. The dampening element receives the pulsatile fluid flow and transforms it into a smoother or more continuous fluid flow.

Figure 2:
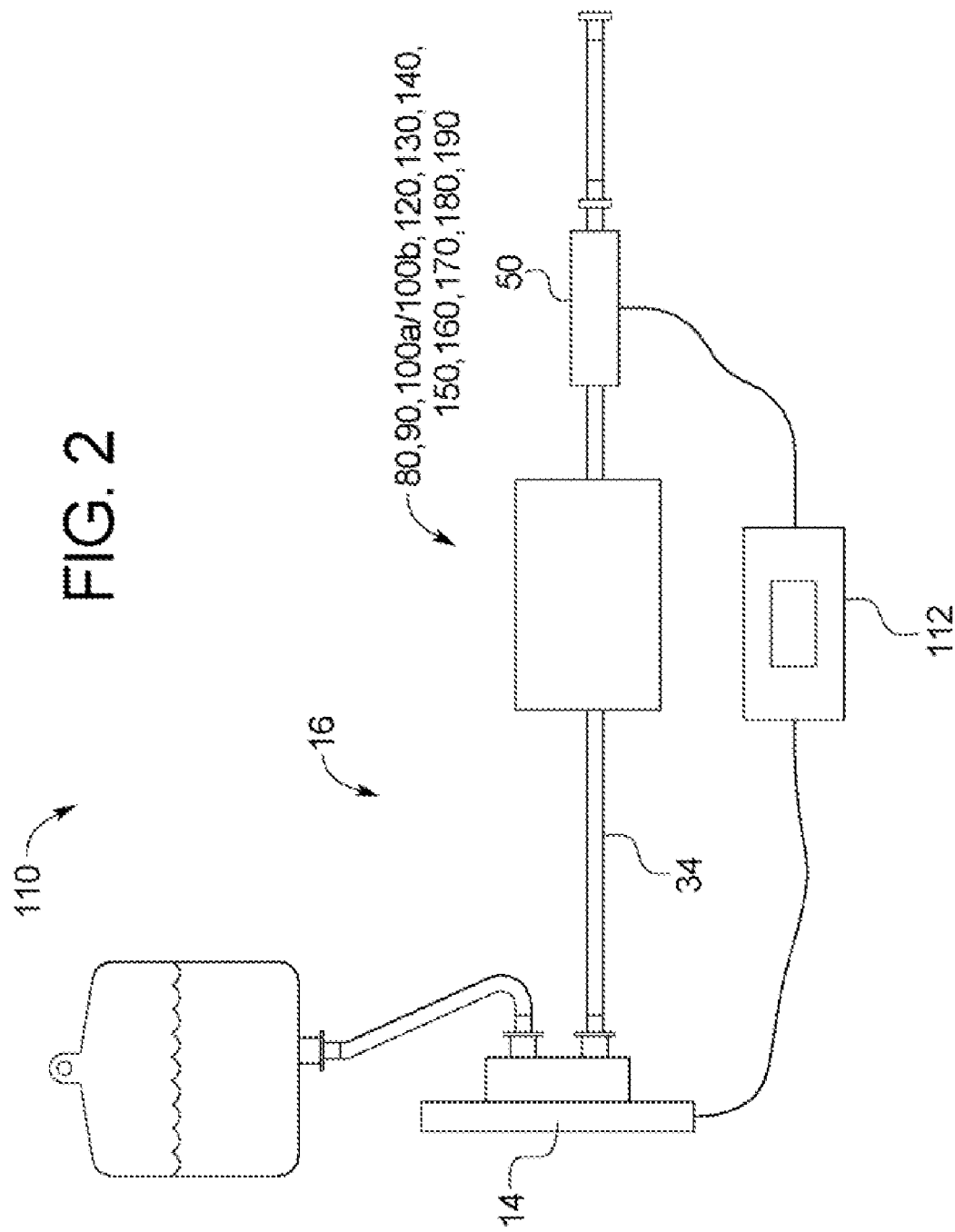
FIG. 2 is a schematic elevation view of one embodiment for placing the various flow pulsatility dampening devices in an infusion system having feedback according to the present disclosure.

Referring now to FIG. 2, infusion system 110 using any of the dampening elements 80, 90, 100a, 100b, 120, 130, 140, 150, 160, 170, 180 and 190 discussed herein includes a control unit 112, which is in communication with the flow sensor 50 and the infusion pump 14. The control unit 112 can be employed to create a closed-loop controlled infusion system that optimizes the flowrate of fluid through the infusion system. For example, a user enters a desired flowrate into the control unit 112. The control unit 112 communicates with the infusion pump 14 to set the pump to pump fluid at the desired flowrate. The control unit 112 receives information from the flow sensor 50 regarding the actual flowrate through the infusion circuit, and then processes the information to calculate the actual flowrate. The control unit 112 can include a proportional/integral/derivative ("PID") type of control that compares the actual flowrate to the desired flowrate and adjusts infusion pump 14 as needed until the actual flowrate is equal to the desired flow rate.

Figure 3:
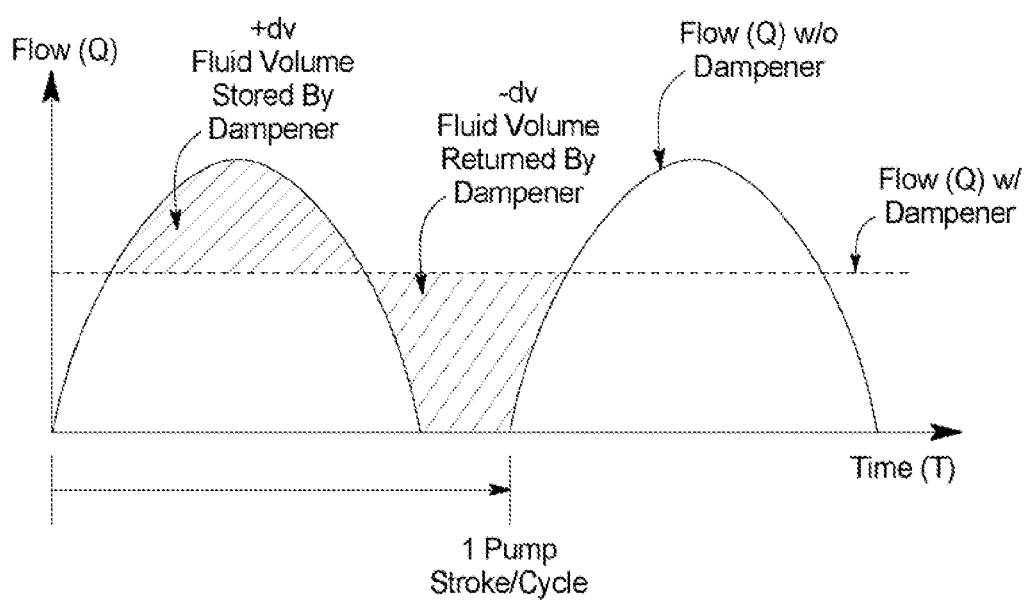
FIG. 3 is a flow per pump cycle schematic illustration of how the flow pulsatility dampening devices of the present disclosure absorb positive pressure pulses and give back flow during negative pressure pulses due to pulsatility inherent in the output of the medical fluid pump of the system of the present disclosure.

Referring now to FIG. 3, the difference dampener embodiments set forth herein use an expandable and/or flexible material that creates expandable or compressible areas in the infusion pathway 16 prior to flow sensor 50. The expandable or compressible areas are responsive to pressure fluctuations caused by the pulsatile fluid flow, which provides a quick-acting response to the fluctuations that results in a smoother and more continuous flow of fluid to flow sensor 50. FIG. 3 shows a dotted line representing a desired dampened Flow (Q) produced via the various dampening embodiment discussed herein. A pulsatile pressure cycle is shown as having positive and negative slopes by the solid line representing "Flow (Q) without dampener". The increasing pressure slope of the pressure cycle, if undampened, causes the medical fluid flowrate to increase above the dotted desired dampened flow line "Flow (Q) with dampener". With dampening, however, the element is instead inflated to store a fluid volume +dv.

When the positive position of the pressure spikes subsides leading to a negative slope of the pressure pulse, such that the solid flow line "Flow (Q) without dampener" would if not dampened fall below the dotted desired dampened flow line "Flow (Q) with dampener", and create a negative volume −dv. The provision of a dampener however allows its expandable and/or flexible material to deflect, giving back stored volume +dv and negating negative volume −dv to smoothen the up to the desired flowrate "Flow (Q) with dampener". The pulsatile pulse cycle just discussed is then repeated per the cyclical nature of the pulsatile flow.

Figure 4:
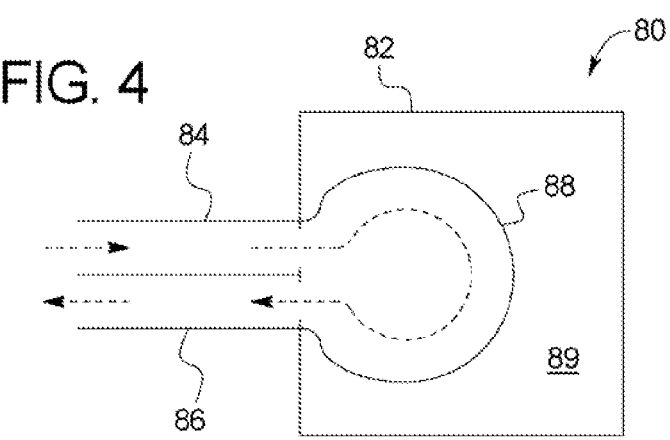
FIG. 4 is a schematic view illustrating one embodiment of a flow pulsatility dampening element of the present disclosure.

Referring now to FIG. 4, one dampener of the present disclosure is illustrated by dampener 80. Dampener 80 includes a housing 82, which can be a disposable, e.g., plastic, housing or a non-disposable housing, e.g., be a permanent component of system 10. Housing 82 includes or defines a medical fluid inlet 84 and a medical fluid outlet 86, which in turn communicate fluidly with infusion line 16 upstream of meter 50. Inlet 84 and outlet 86 in the illustrated embodiment are parallel and adjacent to each other such that medical fluid flow is forced to make a 180° degree turn within a flexible dampening element 88. Inlet 84 and outlet 86 are alternatively inline with respect to each other, such that medical fluid flows into one side of dampening element 88, through inlet 84, and out the opposing side of dampening element 88 through outlet 86. Outlet 86 is alternatively perpendicular to or inline with inlet 84.

Inlet 84 and outlet 86 can be made of any suitable medical grade tubing. Inlet 84 and outlet 86 are alternatively formed integrally with dampening element 88, which is made of a medical grade material that is expandable and compressible. Examples of the medical grade material include: medical grade thermoset elastomers, silicone rubbers, and butyl rubbers. Dampening element 88 swells upon seeing a positive pressure spike to absorb extra volume +dv over each pulsatile pressure pulse illustrated in FIG. 3. The compliant material of chamber 88 contracts upon the depressurization of the pulsatile pressure spike so as to give back +dv through outlet 86 to make up for the lack of volume −dv caused by negative going portion of the pressure wave shown in FIG. 3.

Figure 5:
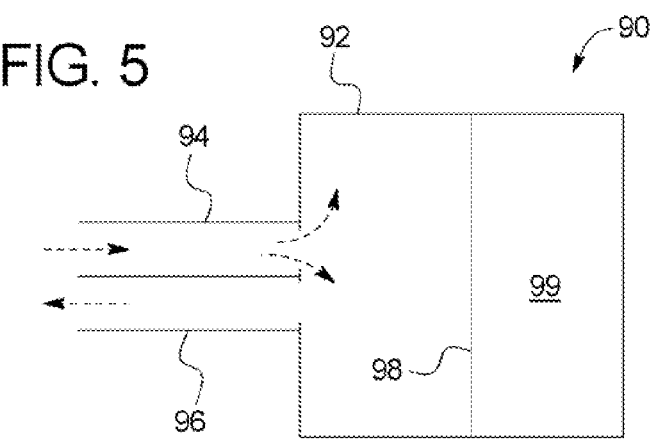
FIG. 5 is a schematic view illustrating a second embodiment of a flow pulsatility dampening element of the present disclosure.

Referring now to FIG. 5, alternative dampener 90 is illustrated. Dampener 90 is similar in many repeats to dampener 80 and includes an outer disposable or permanent housing 92, an inlet 94 and an outlet 86 which in turn communicate fluidly with infusion line 16 upstream of meter 50. Any alternative embodiments discussed above for housing 82, inlet 84 and outlet 86 are applicable to housing 92, inlet 94 and outlet 96. For example, dampener 90, like dampener 80 orients inlet outlet 96 in a direction opposite to the flow though inlet 94. In an alternative embodiment, outlet 96 can extend perpendicular to the flow of fluid through inlet 94 of dampener 90.

Dampener 90 replaces balloon or sack-like chamber 88 above, which expands and compresses radially and spherically, with flexible wall 98, which flexes away from and towards inlet 94 and outlet 96 in a bow-like manner. Flexible wall 98 can be made of any of the materials discussed above for dampening element 88. Upon a positive pulsatile pressure spike, flexible wall 98 bowes or flexes to absorb the extra volume +dv. Flexible wall 98 then un-bowes or un-flexes to a flat condition upon the depressurization of the pulsatile pressure spike, so as to give back positive +dv volume through outlet 96. Giving back the +dv volume through outlet 96 makes up for the lack of volume −dv caused by the negative portion of the pressure spike (see FIG. 3).

Figure 6A:
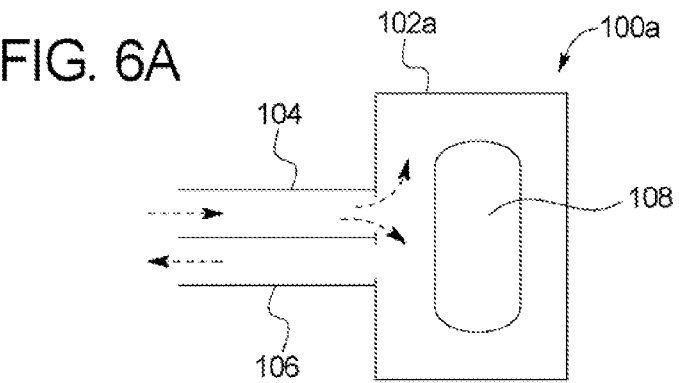
FIGS. 6A and 6B are schematic views illustrating a third embodiment of a flow pulsatility dampening element of the present disclosure.
Figure 6B:
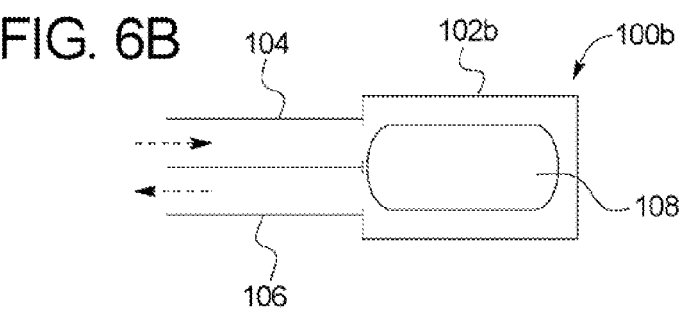

Referring now to FIGS. 6A and 6B alternative embodiments 100a and 100b of yet another dampener of the present disclosure are illustrated. Dampeners 100a and 100b include housings 102a and 102b, respectively, which can be made of any of the materials discussed herein, such as a suitable medical grade plastic. Inlet 104 and outlet 106 for generally vertically housing 102a and generally horizontal housing 102b are formed in the generally parallel, opposite flow manner discussed above, and which in turn communicate fluidly with infusion line 16 upstream of meter 50. Inlet 104 and outlet 106 can be oriented alternatively in a perpendicular or inline manner with respect to each other.

Each housing 102a and 102b houses a highly compressible dampening pouch or balloon 108, forming a dampening element, which is made of a flexible e.g., plastic membrane. Pouch or balloon 108 can be filled with air or a compressible gel. Medical fluid flows around and in contract with balloon 108 as it travels from inlet 104 to outlet 106. In an embodiment, balloon 108 is sized and position so as to have maximum surface area contact with the medical fluid to optimize its dampening effect. Balloon 108 can have a spherical, oval, elliptical or other suitable shape. In one preferred embodiment, balloon 108 is positioned upstream of flow sensor 50.

Upon a positive pulsatile pressure spike, balloon or pouch 108 compresses to absorb the extra volume +dv. Balloon or pouch 108 then decompresses to its natural volume upon the depressurization of the pulsatile pressure spike so as to give back the +dv volume through outlet 106. Giving back the +dv volume makes up for the lack of volume −dv caused by the negative position of the pressure spike (see FIG. 3).

Figure 7:
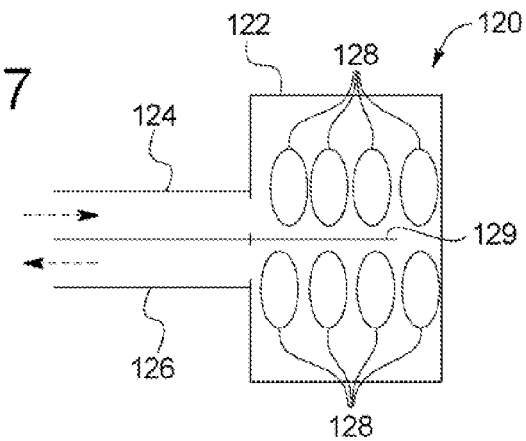
FIG. 7 is a schematic view illustrating a fourth embodiment of a flow pulsatility dampening element of the present disclosure.

Referring now to FIG. 7, dampener 120 illustrates yet another alternative dampener of the present disclosure. Dampener 120 includes a housing 122, which can be made of any of the materials discussed herein. Housing 122 communicates with medical fluid inlet 124 and outlet 126 in any of the alternative ways discussed herein. Inlet 124 and outlet 126 in turn communicate fluidly with infusion line 16 upstream of meter 50.

Housing 122 holds a plurality of compressible air bags or balloons 128, forming a dampening element. In the illustrated embodiment, balloons 128 are split on each side of divider wall 129. Alternatively, divider wall 129 is not provided. As with balloon or pouch 108, balloons or pouches 128 can be filled with air or a compressible gel. Balloons 129 individually and collectively dampen pulsatile medical fluid flow along the outside surfaces of the balloons in a manner consistent with balloon or pouch 108 of dampeners 100a and 100b of FIGS. 6A and 6B, collectively.

Figure 8:
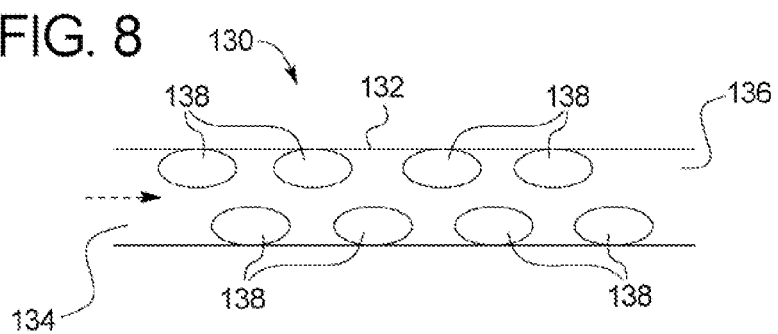
FIG. 8 is a schematic view illustrating a fifth embodiment of a flow pulsatility dampening element of the present disclosure.

Referring now to FIG. 8, dampener 130 illustrates another alternative dampening embodiment of the present disclosure. The analogous housing of dampener 130 is a section of tubing 132 having an inlet and 134 and an outlet end 136. Tubing 132 can be formed integrally with infusion pathway 16, be welded into infusion pathway 16, or be connected to the infusion pathway via connectors, such as union connectors upstream of meter 50.

Tubing 132 holds dampening pouches or balloons 138, forming a dampening element, which operate as described above to dampen pulsatile pressure spikes by compressing and decompressing as medical fluid flows in a pulsatile manner around the balloons. Pouches or balloons 138 can be formed separate from tube 132 or be formed as part of the tube. In the latter instance, for example, balloons 138 can be formed as blister pack or bubble wrap type structures on the inner wall of tube 132.

Referring now to FIG. 9, dampener 140 illustrates yet another alternative pulsatile dampening structure of the present disclosure. Dampener 140 includes a coiled section of infusion line 16, forming a dampening element, which like dampener 130, can be formed integrally with, be spliced into (e.g., welded, heat sealed or ultrasonically sealed) or be connected into infusion line 16 upstream of meter 50. The tubing of coil dampener 140 can be a thin walled compliant plastic, such as silicone. Dampener 140 can rely on one or both of the following to dampen pulsatile flow: (i) the twisting and untwisting of the coils of dampener 140 in response to the positive and negative going slopes of the pressure pulses and (ii) the material of coil 140 being highly compliant such that the wall of the coiled tubing swells and contracts in response to the positive and negative going slopes of the pressure pulses, respectively.

Referring now to FIG. 10, dampener 150 illustrates yet a further alternative pulsatile flow dampening embodiment of the present disclosure. Dampener 150 includes a balloon housing 152, which expands and contracts in response to the positive and negative going slopes of a pulsatile pressure spike, as indicated by the arrowed line. Housing 152 communicates fluidly with inlet 154 and outlet 156, which in turn communicate fluidly with infusion line 16. Inlet 154 and outlet 156 have a 180° degree relationship, as shown, but alternatively have a right-angled or flow through relationship.

Balloons housing includes a plurality of accordion like pleats or walls 158, which can be made of a thin, compliant material, such as any of the materials set forth herein. Walls or pleats 158 expand outward upon seeing the positive slope of the pressure spike and retract upon seeing the negative slope of the spike. The result is a smoothened and dampened medical fluid flow over the entire pressure spike.

Referring now FIG. 11, a flow-through dampener 160 is illustrated. Flow-through dampener includes a flexible chamber 162 that communicates at one end with inlet 164 and a second end with outlet 166, which are formed with, spliced into or connected into infusion line 16. The wall or walls 168 of chamber 162 are made of any of the complaint, medically acceptable materials described herein. Walls 168 expand or flex outward upon seeing the positive slope of the pressure spike and contract upon seeing the negative slope of the pressure spike to provide a smoothened, dampened flow over the entire spike.

Flow-through dampener 170 of FIG. 12 is similar to dampener 160. Here, though, flexible, expandable tubing section 172 has roughly the same diameter as inlet tubing 174 and outlet tubing 176. Dampener 170 functions in a manner consistent with dampener 160.

Figure 13:
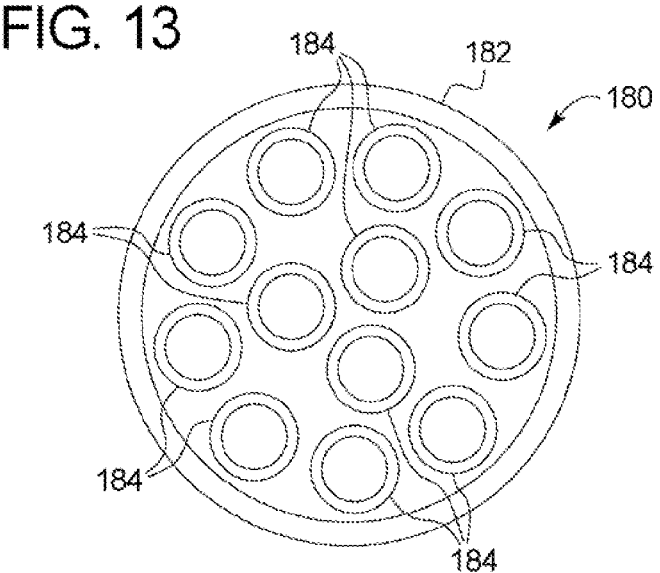
FIG. 13 is a schematic view illustrating a tenth embodiment of a flow pulsatility dampening element of the present disclosure.

Referring now to FIG. 13, dampener 180 illustrates yet a further alternative pulsatile flow dampening embodiment of the present disclosure. Dampener 180 shown in cross-section includes a larger tube (e.g., one to 1.5 inches outside diameter) 182, which can be of any of the materials discussed herein, or be a rigid material that houses a plurality of small diameter tubes 184 (e.g., 0.125 inch diameter), which are of a compliant material, e.g., silicone, in one preferred embodiment. The multiple tubes 184 provide an increased amount of compliant surface area to absorb the pressure spikes. The smaller tubes 184 may also provide an overall restricted flow that also tends to dampen the spike.

Figure 14:
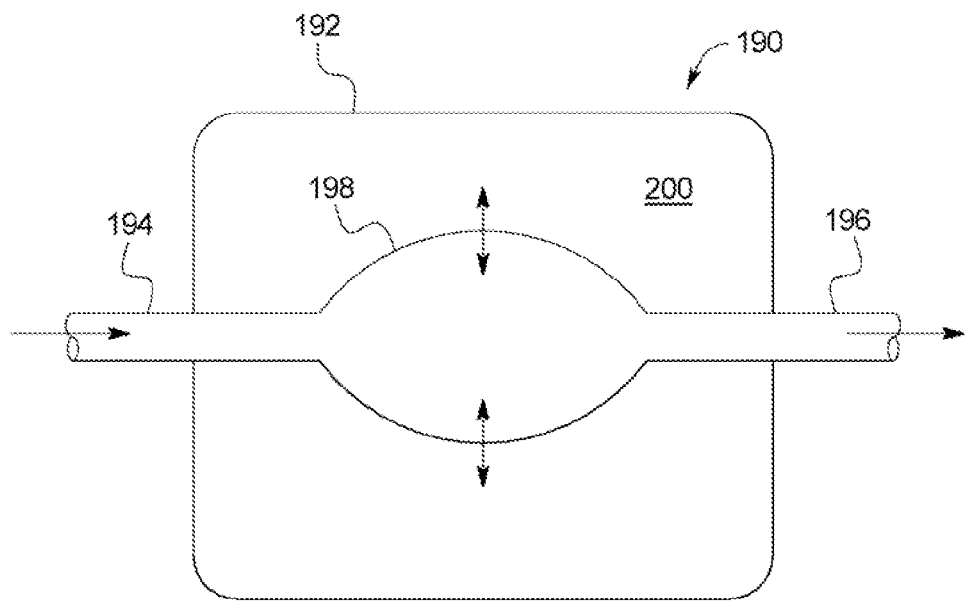
FIG. 14 is a schematic view illustrating an eleventh embodiment of a flow pulsatility dampening element of the present disclosure.

Referring now to FIG. 14, dampener 190 illustrates yet a further alternative embodiment. Dampener 190 includes a housing 192 that sealingly holds a chamber 198 that communicates with an inlet 194 and an outlet 196 in any of the alternative manners described herein. Inlet 194 and an outlet 196 in turn communicate with infusion pathway 16 upstream of meter 50. Housing 192 can be of a rigid material, while chamber 198 is made of any of the flexible expandable materials discussed herein. Housing 192 holds a magneto-rheologiz fluid 200 that surrounds the outside of flexible chamber 198. The magneto-rheological fluid operates by changing it apparent viscosity when subjected to a magnetic field. This change in viscosity of the fluid 200 can be activated to absorb the positive +dv volume and then the viscosity can be increased to give it back during the negative volume −dv portion of the pressure spike.

In an alternative embodiment, magneto-rheologiz material 200 is replaced by compressed air within a pressure holding housing 192, which surrounds flexible chamber 198 for dampening purposes. The compressed air can be from a cylinder, house air or via a pump of infusion pump 14. Compressed air may be injected alternatively into air chamber 89 and/or 99 of dampeners 80 and 90 above in FIGS. 4 and 5, respectively.

If air/gas is used by any of the dampeners discussed herein (either case in which medical fluid flows outside of or inside of a flexible air retaining membrane) as shown in the concepts/embodiments described later, the relationship between the stored fluid volume "dv" shown in FIG. 2, and pressure change can be calculated using the compressed gas law called Boyle's Law:

$$Po*Vo=Pf*Vf=\text{Constant} \quad (\text{Eq1})$$

in which
Po=Original pressure of uncompressed air/gas
Pf=Final pressure of compressed air/gas
Vo=Original volume of uncompressed air/gas
Vf=Final volume of compressed air/gas
Since Vf=Vo−dv by definition, substituting Vf in Eq1 yields $$Po*Vo=Pf*(Vo-dv)$$

$$Po*Vo=Pf*Vo-Pf*dv$$

$$Vo=Pf*dv/(Pf-Po) \text{ or} \quad (\text{Eq2})$$

$$dv=Vo*(Pf-Po)/Pf \quad (\text{Eq3})$$

where Eq2 and Eq3 can be used to determine the volume of air/gas and stored fluid respectively. The total volume "dv" of air/gas needed can be divided/distributed into a suitable number of shapes, forms, or inserts as shown above to create a compact or easily manufactured dampener as shown in the concepts/embodiments described later.

Aspects of the subject matter described herein may be useful alone or in combination one or more other aspect described herein. Without limiting the foregoing description, in a first aspect of the present disclosure, a medical fluid infusion system includes: a fluid pathway for transporting a pulsatile flow of fluid; a dampening element in communication with the fluid pathway, the dampening element configured to actively dampen pressure fluctuations of the pulsatile flow to smoothen the pulsatile fluid flow, the dampening element operable in any orientation; and a fluid flow sensor disposed along the fluid pathway downstream of the dampening element to measure the flowrate of the smoothened fluid flow.

In accordance with a second aspect of the present disclosure, which may be used in combination with the first aspect, the infusion includes a pulsatile infusion pump in communication with the fluid pathway, the infusion pump causing the pulsatile fluid flow.

In accordance with a third aspect of the present disclosure, which may be used in combination with the second aspect, the infusion includes a control member operable with the fluid flow sensor and the infusion pump, the control member configured to receive flowrate information from the flow sensor and to adjust the infusion pump based on the flowrate information.

In accordance with a fourth aspect of the present disclosure, which may be used in combination with any one or more of the preceding aspects, the dampening element includes an outer chamber holding air compressed from a compressed air source and an inner chamber holding the pumped fluid.

In accordance with a fifth aspect of the present disclosure, which may be used in combination with any one or more of the preceding aspects, the dampening element includes an outer chamber holding a rheologiz fluid and an inner chamber holding the pumped fluid.

In accordance with a sixth aspect of the present disclosure, which may be used in combination with any one or more of the preceding aspects, the dampening element includes a plurality of pockets formed on an inner wall of a section of tubing to actively provide a dampening force onto the pumped fluid.

In accordance with a seventh aspect of the present disclosure, which may be used in combination with any one or more of the preceding aspects, the dampening element includes a bellows that is expanded by the pumped fluid so as to actively provide a dampening force onto the pumped fluid.

In accordance with an eighth aspect of the present disclosure, which may be used in combination with any one or more of the preceding aspects, the dampening element includes a coiled section of tubing to actively provide a dampening force onto the pumped fluid.

In accordance with a ninth aspect of the present disclosure, which may be used in combination with any one or more of the preceding aspects, the dampening element includes a flexible wall to actively provide a dampening force onto the pumped fluid.

In accordance with a tenth aspect of the present disclosure, which may be used in combination with any one or more of the preceding aspects, the dampening element includes an expandable tube to actively provide a dampening force onto the pumped fluid.

In accordance with an eleventh aspect of the present disclosure, which may be used in combination with any one or more of the preceding aspects, the dampening element includes a plurality of bunched parallel tubes to actively provide a dampening force onto the pumped fluid.

In accordance with a twelfth aspect of the present disclosure, which may be used in combination with any one or more of the preceding aspects, an infusion system includes: a fluid pathway; an infusion pump for pumping a non-continuous flow of fluid through the fluid pathway; a housing enclosing an expandable membrane, an inside of the membrane defining a chamber that is in communication with the fluid pathway, an outside of the chamber within the housing containing a compressible gas that absorbs pressure fluctuations of the non-continuous flowing fluid to smoothen the non-continuous flow, the housing and the chamber operable in any orientation; and a fluid flow sensor disposed along the fluid pathway downstream of the housing, the fluid flow sensor configured to measure a flowrate of the smoothened fluid flow.

In accordance with a thirteenth aspect of the present disclosure, which may be used with any one or more of the preceding aspects in combination with aspect twelve, an inlet and an outlet of the chamber are arranged at least substantially parallel to one another so that the fluid has to change direction after entering the chamber.

In accordance with a fourteenth aspect of the present disclosure, which may be used with any one or more of the preceding aspects in combination with aspect twelve, the expandable membrane is an expandable balloon or an expandable wall.

In accordance with a fifteenth aspect of the present disclosure, which may be used in combination with any one or more of the preceding aspects, an infusion system includes: an infusion pump; a fluid pathway for transporting a pulsatile flow of fluid produced by the infusion pump; a fluid holding compartment having an inlet and an outlet in fluid communication with the fluid pathway; at least one compressible air balloon located inside the fluid holding compartment that tends to dampen fluctuations of the pulsatile flow of fluid; and a flow sensor disposed along the fluid pathway downstream from the fluid holding compartment.

In accordance with a sixteenth aspect of the present disclosure, which may be used with any one or more of the preceding aspects in combination with aspect fifteen, the inlet and outlet of the fluid holding compartment are configured to force the flow of fluid around the at least one compressible air balloon.

In accordance with a seventeenth aspect of the present disclosure, which may be used with any one or more of the preceding aspects in combination with aspect fifteen, the fluid holding compartment houses a dividing wall that separates at least two of the compressible air balloons.

In accordance with an eighteenth aspect of the present disclosure, which may be used with any one or more of the preceding aspects in combination with aspect fifteen, the inlet and outlet of the fluid holding compartment are arranged with respect to each other such that fluid has to change direction after entering the fluid holding compartment.

In accordance with a nineteenth aspect of the present disclosure, which may be used in combination with any one or more of the preceding aspects, an infusion system includes: a medical fluid infusion system includes: an infusion pump that creates at least a semi-pulsatile flow of fluid; a flow sensor disposed downstream from the infusion pump; and a tube for carrying the at least semi-pulsatile flow of fluid from the infusion pump to the flow sensor, the tube enclosing at least one compressible air balloon for smoothing the flow of fluid from the pump to the flow sensor.

In accordance with a twentieth aspect of the present disclosure, which may be used with any one or more of the preceding aspects in combination with aspect nineteen, a surface of the at least one air balloon is the inner wall surface of the tube.

In accordance with a twenty-first aspect of the present disclosure, any of the structure and functionality illustrated and described in connection with FIG. 1 may be used in combination with any one or more of the preceding aspects.

In accordance with a twenty-second aspect of the present disclosure, any of the structure and functionality illustrated and described in connection with FIG. 2 may be used in combination with any one or more of the preceding aspects.

In accordance with a twenty-third aspect of the present disclosure, any of the structure and functionality illustrated and described in connection with FIG. 3 may be used in combination with any one or more of the preceding aspects.

In accordance with a twenty-fourth aspect of the present disclosure, any of the structure and functionality illustrated and described in connection with FIG. 4 may be used in combination with any one or more of the preceding aspects.

In accordance with a twenty-fifth aspect of the present disclosure, any of the structure and functionality illustrated and described in connection with FIG. 5 may be used in combination with any one or more of the preceding aspects.

In accordance with a twenty-sixth aspect of the present disclosure, any of the structure and functionality illustrated and described in connection with FIGS. 6A and 6B may be used in combination with any one or more of the preceding aspects.

In accordance with a twenty-seventh aspect of the present disclosure, any of the structure and functionality illustrated and described in connection with FIG. 7 may be used in combination with any one or more of the preceding aspects.

In accordance with a twenty-eighth aspect of the present disclosure, any of the structure and functionality illustrated and described in connection with FIG. 8 may be used in combination with any one or more of the preceding aspects.

In accordance with a twenty-ninth aspect of the present disclosure, any of the structure and functionality illustrated and described in connection with FIG. 9 may be used in combination with any one or more of the preceding aspects.

In accordance with a thirtieth aspect of the present disclosure, any of the structure and functionality illustrated and described in connection with FIG. 10 may be used in combination with any one or more of the preceding aspects.

In accordance with a thirty-first aspect of the present disclosure, any of the structure and functionality illustrated and described in connection with FIG. 11 may be used in combination with any one or more of the preceding aspects.

In accordance with a thirty-second aspect of the present disclosure, any of the structure and functionality illustrated and described in connection with FIG. 12 may be used in combination with any one or more of the preceding aspects.

In accordance with a thirty-third aspect of the present disclosure, any of the structure and functionality illustrated and described in connection with FIG. 13 may be used in combination with any one or more of the preceding aspects.

In accordance with a thirty-fourth aspect of the present disclosure, any of the structure and functionality illustrated and described in connection with FIG. 14 may be used in combination with any one or more of the preceding aspects.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A medical fluid infusion system comprising:
an infusion pump;
a fluid pathway for transporting a pulsatile flow of fluid from the infusion pump;
a dampening element in communication with the fluid pathway and operably independent from the infusion pump, the dampening element including a flexible fluid-contacting membrane and an enclosed area outside of the flexible membrane containing a compressible gas that absorbs pressure fluctuations of the pulsatile fluid flow to actively dampen the pressure fluctuations and to smoothen the pulsatile fluid flow, the dampening element operable as a fluid flow dampener in any orientation; and
a fluid flow sensor disposed along the fluid pathway downstream of the dampening element to measure the flowrate of the smoothened fluid flow.

2. The infusion system of claim 1, wherein the infusion pump is a pulsatile infusion pump in communication with the fluid pathway, the infusion pump causing the pulsatile fluid flow.

3. The infusion system of claim 2, which includes a control member operable with the fluid flow sensor and the infusion pump, the control member configured to receive flowrate information from the flow sensor and to adjust the infusion pump based on the flowrate information.

4. The infusion system of claim 1, wherein the compressible gas includes air compressed from a compressed air source and an inner chamber holding the pumped fluid.

5. The infusion system of claim 1, wherein the flexible membrane includes an expandable balloon or an expandable wall.

6. An infusion system comprising:
a fluid pathway;
an infusion pump for pumping a non-continuous flow of fluid through the fluid pathway;
a housing enclosing an expandable membrane, an inside of the membrane defining a chamber and that is in communication with the fluid pathway, an enclosed area outside of the chamber within the housing containing a compressible gas that absorbs pressure fluctuations of the non-continuous flowing fluid to smoothen the non-continuous flow, the housing and the chamber operable as a fluid flow dampener in any orientation; and
a fluid flow sensor disposed along the fluid pathway downstream of the housing, the fluid flow sensor configured to measure a flowrate of the smoothened fluid flow.

7. The medical fluid infusion system of claim 6, wherein an inlet and an outlet of the chamber are arranged at least substantially parallel to one another so that the fluid has to change direction after entering the chamber.

8. The medical fluid infusion system of claim 6, wherein the expandable membrane is an expandable balloon or an expandable wall.

* * * * *